United States Patent
Kaler et al.

(10) Patent No.: US 7,631,298 B2
(45) Date of Patent: Dec. 8, 2009

(54) EXTENSIBLE ARCHITECTURE FOR PROJECT DEVELOPMENT SYSTEMS

(75) Inventors: Christopher G. Kaler, Redmond, WA (US); Martyn S. Lovell, Seattle, WA (US); Michael J. Grier, Woodinville, WA (US); Bradley J. Bartz, Lynnwood, WA (US)

(73) Assignee: Microsoft Corporation, Redmond, WA (US)

( * ) Notice: Subject to any disclaimer, the term of this patent is extended or adjusted under 35 U.S.C. 154(b) by 592 days.

(21) Appl. No.: 11/171,768

(22) Filed: Jun. 30, 2005

(65) Prior Publication Data

US 2005/0240640 A1    Oct. 27, 2005

Related U.S. Application Data

(63) Continuation of application No. 09/717,537, filed on Nov. 21, 2000, now Pat. No. 6,915,507.

(51) Int. Cl.
G06F 9/44    (2006.01)
(52) U.S. Cl. .................................................. 717/120
(58) Field of Classification Search ................ 717/122, 717/151, 174, 101–117, 120; 709/201, 203, 709/217, 220, 223; 707/2, 4, 5, 8; 725/46; 705/1, 37, 54; 715/202, 209, 234, 738, 763
See application file for complete search history.

(56) References Cited

U.S. PATENT DOCUMENTS

| | | | |
|---|---|---|---|
| 5,574,898 A * | 11/1996 | Leblang et al. ............... 707/1 |
| 5,649,200 A | 7/1997 | Leblang et al. ............ 395/703 |
| 5,862,325 A | 1/1999 | Reed et al. ............. 395/200.31 |
| 5,978,579 A | 11/1999 | Buxton et al. ............... 395/701 |
| 6,094,654 A * | 7/2000 | Van Huben et al. ............ 707/8 |
| 6,216,140 B1 | 4/2001 | Kramer ...................... 707/511 |
| 6,523,027 B1 | 2/2003 | Underwood ................... 707/4 |
| 6,701,310 B1 * | 3/2004 | Sugiura et al. ................. 707/5 |
| 6,925,608 B1 * | 8/2005 | Neale et al. ................. 715/763 |
| 7,020,697 B1 * | 3/2006 | Goodman et al. ........... 709/223 |
| 7,200,640 B1 * | 4/2007 | Cole et al. ................... 709/217 |
| 2002/0019827 A1 * | 2/2002 | Shiman et al. ............. 707/200 |
| 2005/0055306 A1 * | 3/2005 | Miller et al. .................. 705/37 |
| 2005/0278741 A1 * | 12/2005 | Robarts et al. ................ 725/46 |

FOREIGN PATENT DOCUMENTS

JP    09-198393    7/1997

OTHER PUBLICATIONS

Gary Marchionini, Augmenting Library Services: Toward the Sharium', Proceedings of International Symposium on Digital Libraries, 1999, pp. 1-8 (see attach: Sharium_Marchionini.pdf).*
Bibliographic data, "Augmenting Library Services" 2 pages ( see attach: Marchionini_BiB.pdf).*

* cited by examiner

Primary Examiner—Tuan Anh Vu
(74) Attorney, Agent, or Firm—Woodcock Washburn LLP

(57) ABSTRACT

A software-development system or versioning system has a collection of modules for performing individual development functions such as document editing, keyword processing, and private-copy management. Each module has an interface compatible with that of the others, so that modules can be added to or substituted for the original modules, if the new modules conform to the interface. The architecture of this system supports the performance of development actions such as document merging and keyword expansion at any location within the system. The system operates upon documents and files as objects in an object space, rather than in name spaces.

16 Claims, 6 Drawing Sheets

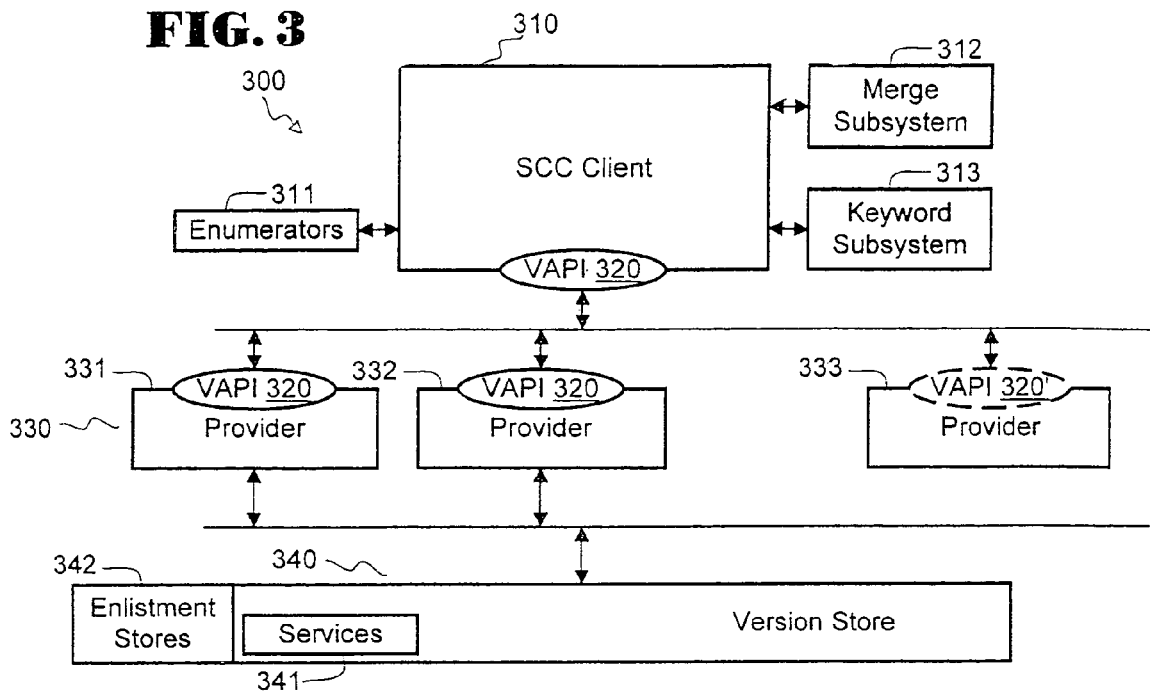
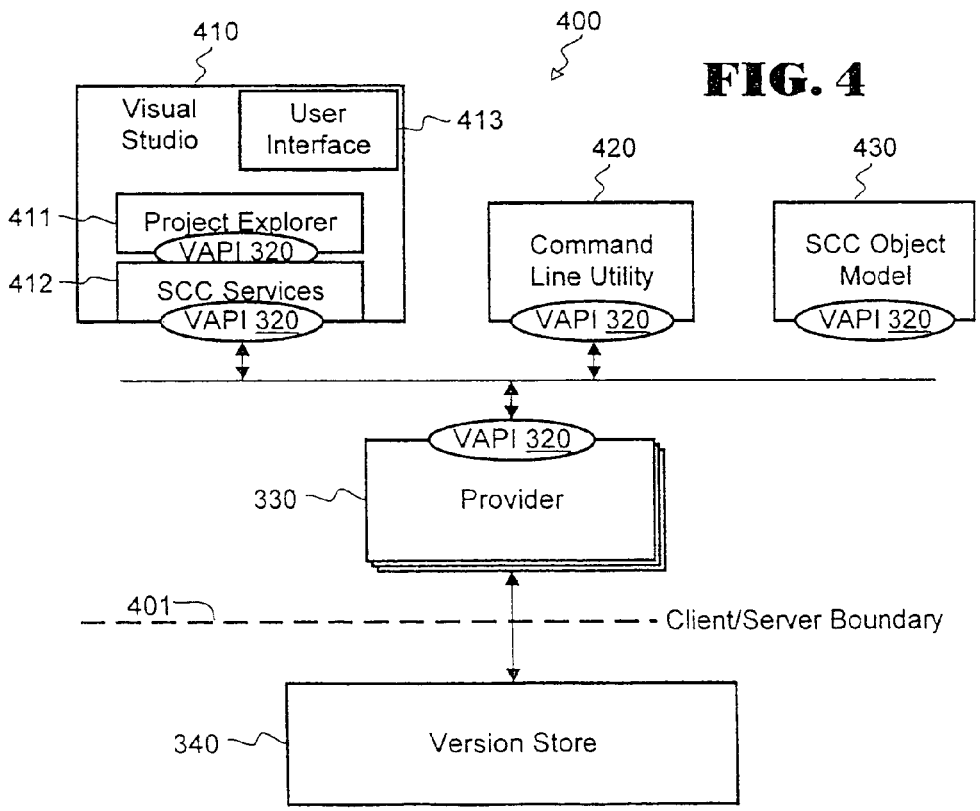

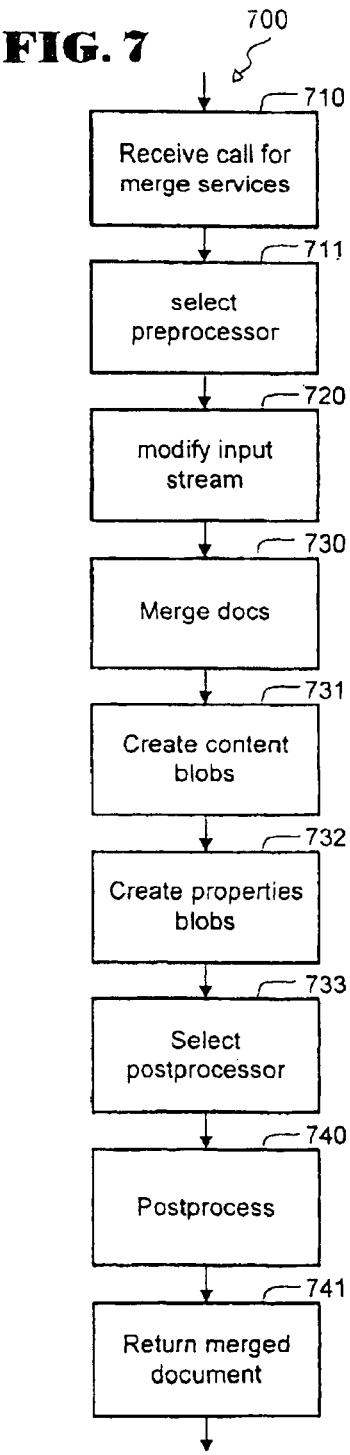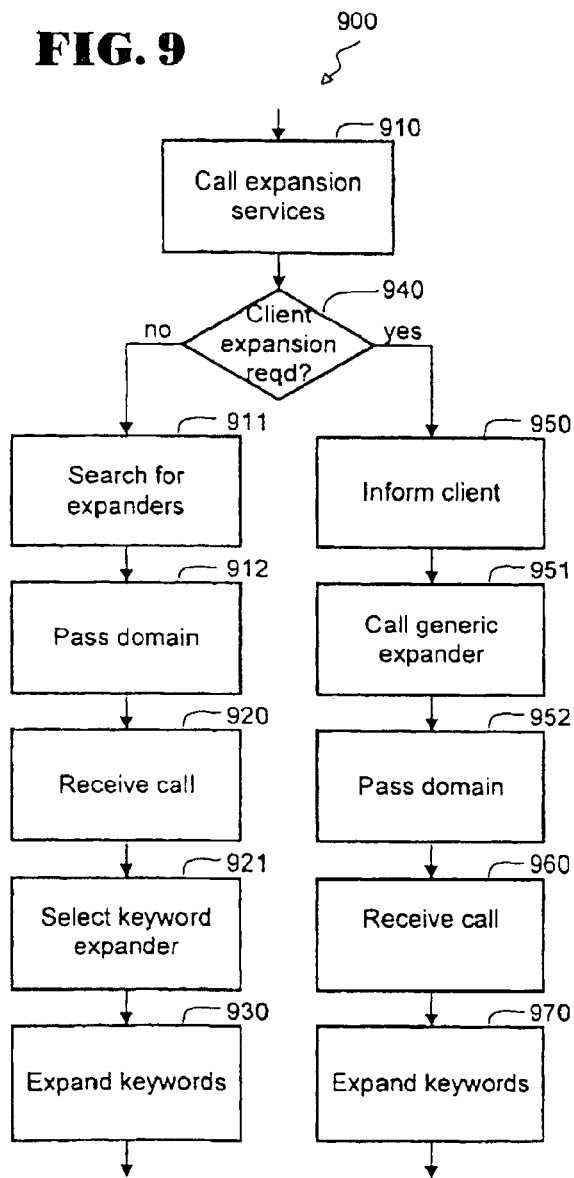

EXTENSIBLE ARCHITECTURE FOR PROJECT DEVELOPMENT SYSTEMS

CROSS-REFERENCE TO RELATED CASES

This application is a continuation of U.S. patent application Ser. No. 09/717,537 filed on Nov. 21, 2000, now U.S. Pat. No. 6,915,507 entitled "Extensible Architecture for Project Development Systems."

TECHNICAL FIELD

The present invention relates to electronic data processing, and more particularly concerns a system architecture for managing many documents or files that may assume different versions over the life of a project such as computer program development.

BACKGROUND

Complex projects of any kind involve the cooperation of large numbers of individuals and groups working on even larger numbers of interdependent items. In particular, the development of application programs, operating systems, and other computer software commonly involves hundreds or thousands of people and documents numbering several orders of magnitude higher, over time periods of months and years.

A major part of managing large projects concerns systems for controlling different versions of versioned items documents and files. In program development, a source-code control system typically includes several pieces, almost always including a storage that provides efficient versioned storage of files, a differencing/merging engine for combining different versions of the same file, modules for operating upon multiple file formats such as text and graphics documents, and user interfaces for various parts of the system, including those for differencing and merging.

To integrate heterogeneous control systems into a useful development tool requires an architecture for integrating the many individual parts with a high degree of concinnity. The organizing force of a software architecture resides in the interfaces among the parts of the overall system. Interfaces are commonly implemented as application program interfaces (APIs). Traditional integration efforts coped with the depth and diversity of available source-control systems by defining a high-level API that abstracts both storage operations and user interfaces. For example, Microsoft Corp. integrated these functions into its own development tools using an interface called MSSCCI (Microsoft Source Code Control Interface). This interface proved inflexible, provided a limited model of the underlying data, and was unable to solve a broad range of important problems. This interface cannot mix pieces from different providers for performing other functions, or for performing existing functions in a different manner. Its design was not future-proof.

Another problem with traditional integration APIs is that they are based upon server namespaces. That is, an object is referred to by its path name and file name on the server that stores the files under development. This makes it hard to rename files. The API cannot determine that a reference to a file called 'New' refers to the same file that had been called 'Old'. This was a problem even when all that was stored was source code, and traditional systems often disallowed name changes altogether. However, newer systems based on the World Wide Web require the names of objects to change often.

Existing development APIs have also been limited in their support for different kinds of files. They abstract the calculation of differences and merges as part of the storage. The types of files understood were bound into the products, and could not be extended by third parties so as to create new file formats. This problem becomes more important as Web-based systems grow in popularity. The Web employs many types of files, and no single system can address all of these formats, now or in the future. For Web-style projects, namespaces are a primary element of the software system. Moreover, traditional integration APIs provide no semantic support for parallel development. Users must manage their own copies of different versions of their projects.

The MSSCCI architecture mentioned above is widely supported in the software-development industry despite the fact that it remains a private interface without any formal standard. This and other available interfaces only support a small portion of the typical source-code control functions. They are not extensible to additional functions or formats, and they cannot be combined in mix-and-match combinations. Other current efforts address APIs and protocols for communicating with "version stores"—mechanisms for holding multiple versions of documents and files. None of the conventional systems provide a deep or consistent way for substituting third-party differencing and merging technologies into the versioned environment. This lack of any extensible architecture has hindered the development of versioning, especially for document management, where file formats are diverse and numerous, and where designers seldom work together with the organizations that produce version stores. Although some existing systems provide core support for object-based (rather than namespace-based) storage, they do not expose this capability deeply within their organization, if they have any extensibility at all.

SUMMARY

The present invention offers an architecture for extensible systems for managing projects having many individual versioned items. Because the described embodiments relate to software-development projects, the items will be referred to as "documents" or synonymously as "files."

Systems constructed according to the present architecture include a collection of modules for providing individual development services or functions. A client module processes user data and commands, and coordinates the operation of the service-provider modules. The term "user" herein refers broadly to a person, or to another program or system of any kind that can initiate commands to the client module.

Each module has a mutually compatible interface. Thus, modules not in the original system can be added or substituted for one or more of the original modules, as long as all of them are compatible with the same system-wide interface. Each of the elements of the system can be individually replaced or extended, and the architecture supports the performance of functions at any place in its environment. Further, the interface operates upon documents and files as objects in an object space, rather than in one or more name spaces. A version store for the documents communicates with at least some of the service providers, and can optionally be implemented as a database.

The architecture can implement the set of interfaces as an application program interfaces (API) that the client and the service providers all employ, although other implementations are possible. Part or all of the API can be built specifically for use in this architecture, or it can be adapted from other environments.

Aspects of the invention include a development client program, a number of development service providers, and a version store for holding development documents. The client receives commands from a user and passes them over its interface to compatible interfaces architected in the service providers. The multiple development service providers each have code for performing a development function, and an interface that is compatible with all the other service providers, so that they can be individually plugged into and unplugged from the system in any combination. A merge subsystem has, in addition to a merge engine, a merge broker for selecting among a number of selectable preprocessor modules, and optionally also has multiple postprocessors. A keyword-expansion subsystem has a keyword broker for selecting among multiple keyword-expansion modules for different domains of keywords in different documents.

DRAWING

FIG. 3 is a block diagram of a versioning system according to the invention.

FIG. 4 shows the versioning system of FIG. 3 in a product setting.

FIG. 7 is a flowchart of the operation of the subsystem in FIG. 6.

FIG. 9 is a flowchart showing the operation of the subsystem in FIG. 8.

DETAILED DESCRIPTION

This description and the accompanying drawing illustrate specific examples of embodiments in which the present invention can be practiced, in sufficient detail to allow those skilled in the art to understand and practice the invention. Other embodiments, including logical, electrical, and mechanical variations, are within the skill of the art. Skilled artisans will also recognize features and advantages of the invention other than those explicitly set forth. The scope of the invention is to be defined only by the appended claims, and not by the specific embodiments described below.

In the following description, Section 1 presents illustrative computer hardware and software environments capable of hosting the invention. This section includes an overview of an API that can be employed in implementing the invention. Section 2 describes an architecture of a software-development system organized according to the invention. Section 3 further details a number of development service providers having novel features in connection with the invention.

1. Environment

Figure 1:
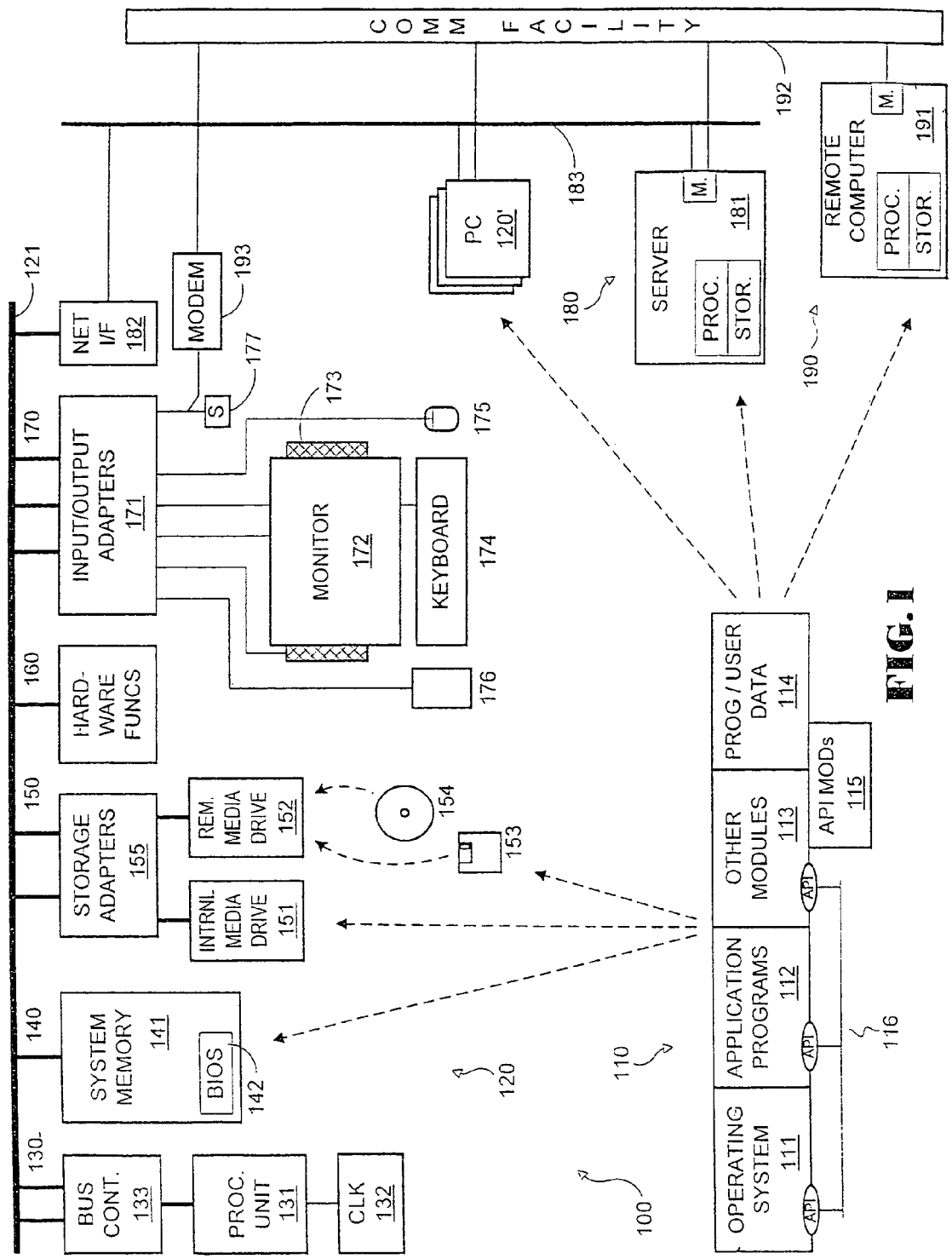
FIG. 1 is a high-level block diagram of an illustrative environment in which the invention can be practiced.

FIG. 1 is a high-level diagram of an illustrative environment 100 having software 110 and hardware 120 for hosting the invention as executable instructions, data, and/or electronic and mechanical components. Other suitable environments, and variations of the described environment are also possible.

Hardware components 120 are shown as a conventional personal computer (PC) including a number of components coupled together by one or more system buses 121 for carrying instructions, data, and control signals. These buses may assume a number of forms, such as the conventional ISA, PCI, and AGP buses. Some or all of the units coupled to a bus can act as a bus master for initiating transfers to other units. Processing unit 130 may have one or more microprocessors 131 driven by system clock 132 and coupled to one or more buses 121 by controllers 133. Internal memory system 140 supplies instructions and data to processing unit 130. High-speed RAM 141 stores any or all of the elements of software 110. ROM 142 commonly stores basic input/output system (BIOS) software for starting PC 120 and for controlling low-level operations among its components. Bulk storage subsystem 150 stores one or more elements of software 110. Hard disk drive 151 stores software 110 in a nonvolatile form. Drives 152 read and write software on removable media such as magnetic diskette 153 and optical disc 154. Other technologies for bulk storage are also known in the art. Adapters 155 couple the storage devices to system buses 121, and sometimes to each other directly. Other hardware units and adapters, indicated generally at 160, may perform specialized functions such as data encryption, signal processing, and the like, under the control of the processor or another unit on the buses.

Input/output (I/O) subsystem 170 has a number of specialized adapters 171 for connecting PC 120 to external devices for interfacing with a user. A monitor 172 creates a visual display of graphic data in any of several known forms. Speakers 173 output audio data that may arrive at an adapter 171 as digital wave samples, musical-instrument digital interface (MIDI) streams, or other formats. Keyboard 174 accepts keystrokes from the user. A mouse or other pointing device 175 indicates where a user action is to occur. Block 176 represents other input and/or output devices, such as a small camera or microphone for converting video and audio input signals into digital data. Other input and output devices, such as printers and scanners commonly connect to standardized ports 177. These ports include parallel, serial, SCSI, USB, FireWire, and other conventional forms.

Personal computers frequently connect to other computers in networks. For example, local area network (LAN) 180 connect PC 120 to other PCs 120' and/or to remote servers 181 through a network adapter 182 in PC 120, using a standard protocol such as Ethernet or token-ring. Although FIG. 1 shows a physical cable 183 for interconnecting the LAN, wireless, optical, and other technologies are also available. Other networks, such as wide-area network (WAN) 190 can also interconnect PCs 120 and 120', and even servers 181, to remote computers 191. Computers 181 and 191 have processors, storage, and communications equipment similar to those of PC 120, although usually of higher capacity. FIG. 1 illustrates a communications facility 192 such as a public switched telephone network for a WAN 190 such as an intranet or the internet. PC 120 can employ an internal or external modem 193 coupled to serial port 177. Other technologies such as packet-switching ISDN, ATM, DSL, frame-relay are also available. In a networked or distributed-computing environment, some of the software 110 may be stored on the other peer PCs 120', or on computers 181 and 191, each of which has its own storage devices and media.

Software elements 110 may be divided into a number of types whose designations overlap to some degree. For example, the previously mentioned BIOS sometimes includes high-level routines or programs which might also be classified as part of an operating system (OS) in other settings. The major purpose of OS 111 is to provide a software environment for executing application programs 112 and for managing the resources of system 100. An OS such as Windows® or Windows NT® from Microsoft Corp. commonly includes high-level application-program interfaces (APIs), file systems, communications protocols, input/output data conversions, and other functions.

Application programs 112 perform more direct functions for the user. A user normally calls them explicitly, although they can execute implicitly in connection with other applications or by association with particular data files or types. Modules 113 are packages of executable instructions and data which may perform functions for OSs 111 or for applications 112. Dynamic link libraries (.DLL) and class definitions, for instance, supply functions to one or more programs. Data 114 includes user data of all types, data generated and/or stored by programs, and digital data that third parties make available on media or by download for use in computer 120. Software elements can be embodied as representations of program instructions and data in a number of physical media, such as memory 140, non-volatile storage 150, and signals on buses 183, 192, etc.

Application programming interfaces (APIs) frequently serve as interfaces in software systems, and are symbolized by the small ellipses 116 in FIG. 1. An API is a contract between two or more independent pieces of software. This contract takes the form of a protocol between the pieces. The protocol specifies what functions may be requested by one piece from another piece. It specifies a format for transmission of the request (which might include commands, parameters, and other data), and a format for the return of any results or errors from the request. APIs can be implemented in a number of ways, including machine-code addresses, static libraries, DLL (dynamic link library) entry points, COM (component object model) interfaces, textual command languages, or any mixture of these modalities. Any software model or object model that is capable of describing the contract between two programs, objects, or other software is capable of representing an API. Additionally, an API can be expressed in a completely non-software-related fashion, for example as a set of imperative recipes expressed in a language such as English. APIs are frequently defined in an abstract interface-definition language (IDL), and in related documentation.

An API generally offers an entire set of functions that are called individually. An API contract can, however, have optional features. That is, a software module might not implement all of the functions of the entire API definition, because it cannot perform some of the functions of the full API, because it does not need to invoke certain functions, or for other reasons. Such subsetting of an API provides a convenient way to allow diversity in the contracting software modules, and allows some participants in an API contract to have more limited participation than other participants in the same contract, while still remaining compatible with them. A module is compatible with an API or other interface if it conforms to those of the interface definitions in the set that it needs in order to communicate data that that module processes or communicates to and from other modules in the system. An API definition can state explicitly that some of its parts are required for every module that uses it, while other parts are optional, providing additional functionality for those modules that choose to use them.

Figure 2:
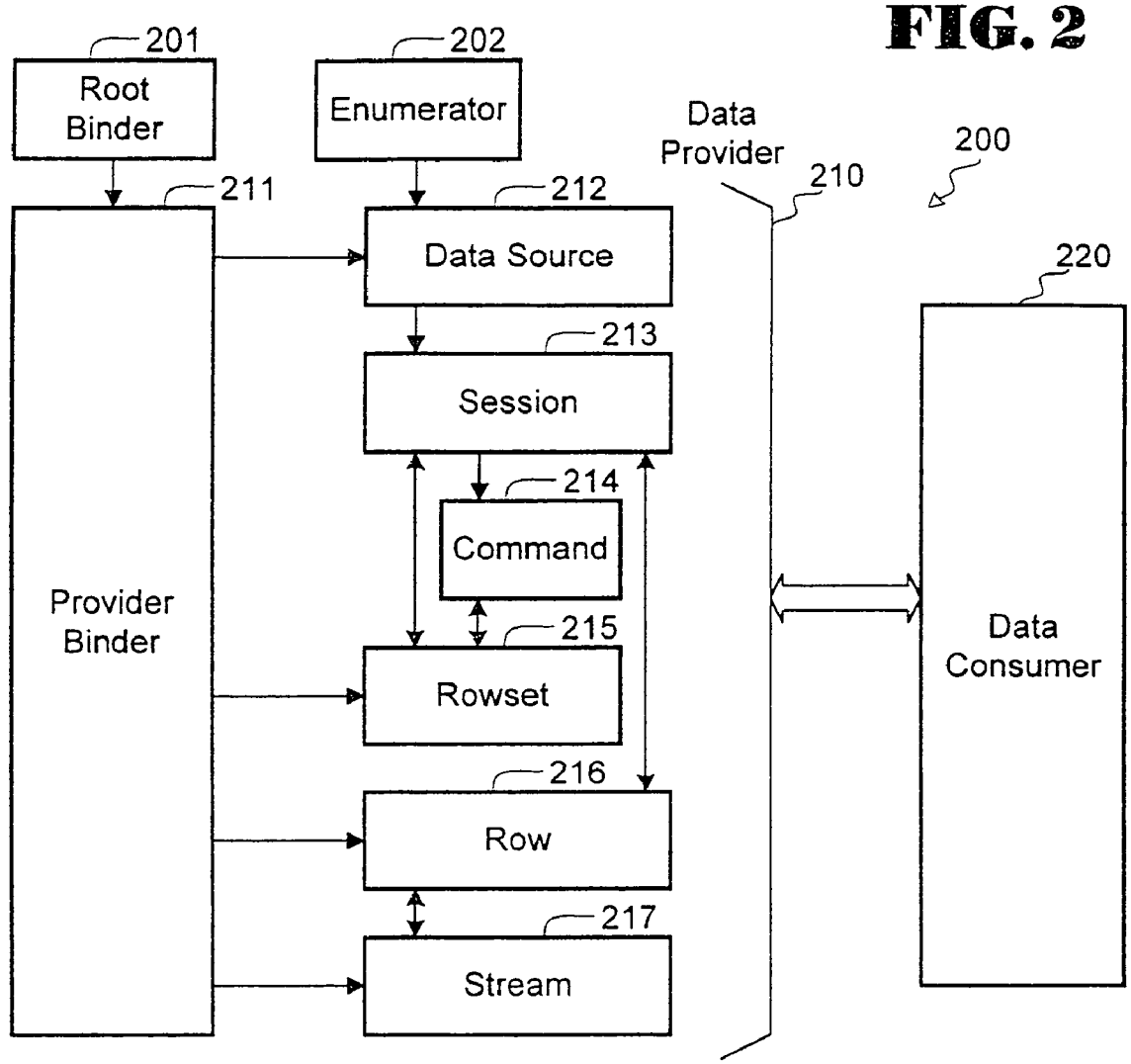
FIG. 2 is a block diagram representing the operation of an application program interface employed in an embodiment of the invention.

FIG. 2 is a diagram 200 representing the overall structure of an illustrative API that can be easily adapted for use as an interface serving the invention. Available publicly from Microsoft Corp., OLE DB (literally, Object Linking and Embedding database), is an API for use with databases. In this context, OLE is a synonym for COM (Component Object Model), a generic abstract mechanism from Microsoft Corp. for expressing APIs. OLE DB is thus a specific API, targeted for generic contracts between database systems and programs in a database system. OLE DB includes a comprehensive set of interface methods for storing, finding, retrieving, and performing other conventional operations upon data and other objects located in a variety of storage devices in one or more computers. It has the ability to manage many different types of data, including structured data such as relational databases, partly structured data such as file systems, and unstructured data such as documents.

The OLE DB API implements an overall interface between a data provider 210 and a data consumer 220. Both of these are software that manages certain types of data. A data provider directly exposes data to the consumer via the interfaces. Other providers provide services such as query processing, and do not themselves expose data. In general, a data store acting as a data provider need not necessarily support or expose all of the OLE DB interfaces, although it must of course support the native functions of the data types that it manages. A data consumer can choose any desired level of interoperability with specific data providers, and can sometimes even consume more than the provider itself supports, if a service provider having the missing functionality is available. A consumer can query a provider to determine its capabilities.

A binder is an OLE DB object that binds resources named in a URL (universal resource locator) to an OLE DB object. Binding involves associating a column of a row, set or a parameter of a command with a variable; a binding denotes the association itself, or a structure that describes the association. Patent application Ser. No. 09/717,533, now issued as U.S. Pat. No. 6,842,904, also describes binders. Root binder 201 is an object that oversees the direct binding process. It maps bind requests to particular data providers such as 210. Provider binder 211 is an object that performs direct binding operations on the URL namespace for which it is registered. It creates particular objects based upon the URL specified in the bind request.

An OLE DB enumerator is an object that retrieves information concerning a provider that is available on the system. In the Windows® operating systems from Microsoft Corp., much of this information is contained in a registry, and can be accessed thence directly if desired. However, an enumerator abstracts the source of the information from an application, making it reachable regardless of where it is actually kept. Enumerator 202 obtains a particular data source object 212 named in a bind request to provider 210. A data source object connects to a data store such as a database, file, or document that a user wishes to access. Sessions 213 can then be created against the data source. A session is an individual connection that persist over a time until it is explicitly closed. Particular requests during a session can obtain commands 214, rowsets 215, and rows 216. A command 214 in a data-manipulation language issued during a session can obtain one or more rowsets. Rowsets can be used to navigate to a single row or to a data stream 217. A rowset, in OLE DB as in relational database parlance in general, is an object that contains one or more rows each having columns of data that satisfy a criterion in a query or other request. A row is a set of related columns that describe a specific entity. A data stream is data that encapsulates arbitrary data, and may contain a document, a file, or other data in any format or in none. Rowsets can be used to navigate to a particular row and then to a stream containing, e.g., a document.

2. Versioning Architecture

The embodiment described below implements a versioning API (VAPI) within the OLE DB framework. The use of a database framework such as OLE DB as a foundation for a versioning system has several advantages. Version files are commonly written in the format of documents. Such development documents commonly represent source code in high-level programming languages, header files containing information about the programs under development and their relationships to each other, assembly code, executable binary code, interfaces and their definitions, libraries, relational data and schemata, components, interfaces, forms, program manifests, registry structures and contents, web pages, scripts, forms, images, sound files, metadata, and other kinds of data. The present invention, however, is entirely agnostic as to types, and can accommodate any kind of document or file type. OLE DB supports the concept of a document as an object that it can manipulate. It includes facilities for tagging them as to type, so that the appropriate programs for processing them can be selected. Adding semantics for the additional processes required for versioning does not involve any distortions of the underlying mechanisms of OLE DB. Abstractions such as enumerators, data sources, and sessions in OLE DB can be mapped in a direct manner to services required from a versioning provider. OLE DB has a well-defined set of services for locating rows and documents, and for performing queries and returning arbitrarily large results. Other database systems as well have some of these attributes, and would also be candidates for constructing a versioning system according to the present invention.

Past versioning systems store and retrieve documents as files having names and paths in directory trees in particular computers. In some settings, such as the World Wide Web, names change frequently, and namespace-based retrieval can often fail to find a desired document. In this embodiment, documents are stored in a database, which permits retrieval with queries designating characteristics that can be associated with the documents, in a database row or other mechanism. Accordingly, each document in the system is given a unique object identifier. The path and name of the document are also associated with the document, thus allowing retrieval either by unique identifier or by namespace-based file names. Because the OLE DB-based VAPI operates in a fundamental way upon the database paradigm, any VAPI function has the ability to query a document by any defined characteristic, such as its name, even though the actual file-system name or server namespace might have changed in the meanwhile. When users make isolated changes to an object, such as renaming it, they are still able to refer unambiguously to the appropriate object, because the VAPI provides names and abstractions for their isolated changes. Thus, documents in the invention can be namespace-neutral in a deep manner, throughout every part of the versioning system.

Versioning systems also limit the types of documents that they support, and do. not offer extensibility to other types in a simple or natural manner. Because the present system employs a database paradigm at its core rather than a file-system model, a document can be treated as an encapsulated black box or blob whose contents are irrelevant to any function that needs only to handle it as an entity. The type of the document is encoded as a characteristic associated with the document. When an API function retrieves a document and its associated characteristics, the document type can be interrogated, and appropriate action taken, such as routing the document to an editor that understands that type of document. If a function desires to retrieve only a certain document type, then that type can be specified in a query. New document types can be added merely by assigning them additional codes in a particular field or column of a database row associated with the document. The ability to handle new types of documents at the system level becomes important in World Wide Web development, where file types proliferate for different kinds of data.

Moreover, a database model for the VAPI allows further document characteristics to be enrolled as new columns or fields in the records or rows associated with the documents.

FIG. 3 is a high-level diagram of the overall architecture of a versioning system of the invention. A source-code control (SCC) client 310 directs the system 300. It receives commands from a user for performing development functions and sequences of operations, usually in connection with one or more specified development documents. It coordinates system 300 by interacting with enumerators 311 registered on system 100, FIG. 1, to discover which data providers and service providers are available for versioning operations. These enumerators might point to service providers located in one or more of the computers 120, 120', 180, and 190. Client 310 employs one or more merge subsystems 311 to perform merge/differencing operations. These operations involve the combination of two or more different versions of a document to form a single document. The terms "merge" and "differencing" are very closely related, and these terms are used interchangeably herein; they refer to determining the differences between documents, flagging conflicts, and possibly resolving them to form a merged output document. Client 310 also employs a keyword subsystem 313 to detect and process embedded keywords. Merge and keyword operations can be requested from any point in system 300, such as from the providers and stores described below.

Client 310 interacts via versioning interface (VAPI) 310 with multiple individual providers 330 of versioning services. Interface 320 is a collection of individual API methods largely taken from the publicly available Microsoft OLE DB interface, plus methods added specifically for versioning functions. This interface forms the entire set of interactions between client 320 310 and all of the versioning service providers 330. Alternatively, interface 320 could be fashioned from some other existing collection of API methods, could be constructed exclusively for this purpose, or could be implemented in a form other than an API. The important point is that the contract provided by the interface can be understood and followed by the client and by all the service providers, at least to the extent necessary to communicate commands and data to other modules in the same system. That is, the interface can in some cases be subsetted and still remain compatible.

Individual ones of the providers, such as 331-333, offer query processing, enlistment management (defined below in conjunction with FIG. 10), and other conventional versioning functions. Some or all of the providers 330 communicate with a version store 340 that holds documents and/or other objects that constitute the entity being developed by the overall system, for storing and retrieving the documents. Although FIG. 3 shows only one store, architecture 300 permits multiple version stores within the same system, all having the same interface, and thus able to communicate with any other block in the system. The data store can also offer some common services, indicated at 341; to providers 330 and to client 310, if desired. Direct providers such as 331 and 332 communicate with version store 340 via a conventional interfaces, although it is possible that they could use the VAPI interface instead. Direct providers map requests from the client, such as "get" and check-in" onto operations against the version store for storing, retrieving, and otherwise manipulating documents in response to user requests. Enlistment-manager providers communicate with one or more enlistment stores 342; these can be physically part of a version store, or separate stores in a server or in other computers.

The invention thus employs a single interface among all service providers and the client. In this embodiment, that interface is a collection of interface operations from the OLE DB standard. Therefore, a provider such as 331 that performs query processing can be unplugged from system 300 and replaced by a completely different processor that offers the same set of services, more query services, or different query services, merely by registering an enumerator for the new provider. Third-party vendors can offer versioning services of new kinds by constructing the interfaces of their providers to be compatible with the single VAPI 320. Not all providers need recognize the entire VAPI set of interface operations. Provider 333, for example might provide only limited operations that do not require all of the methods of the full interface, such as file branching or labeling. Its VAPI 320', is shown in dashed outline to indicate that it does not provide the full interface. While the interface methods that it does provide are the same as those of the full interfaces 320, it does not provide the entire set of these methods.

FIG. 4 illustrates a versioning system 400 in a product setting example. A program 410 provides a number of functions in addition to elementary versioning, such as facilities 411 for parallel development by multiple groups. An SCC services module 412 includes a client such as 310, FIG. 3, that makes use of enumerators, merge engines, and service providers. Module 412 communicates with a user via a user interface 413 (using I/O devices such as 170, FIG. 1) integrated with that for the overall program 410 for receiving user commands, displaying system results and documents, etc. A shared command-line utility 420 writes commands to the system. The command-line utility can be used with any VAPI-compliant service provider without special modification. Third-party provider vendors can extend or replace utility 420 in order to access any additional or special capabilities of their providers. System 400 further includes a shared object model 430 to make it easier for third-party vendors to build providers and other objects in the system. An object model in general affords more direct access to feature sets of programs, and avoids complications such as going through dialogs or other additional constructs in the programs. An object model for a versioning system can abstract from the full VAPI 320 to provide a programmability interface for macros and other control applications. As with utility 420, vendors can extend the object model to include further aspects of the full VAPI, or even of an extended VAPI. Line 410 in FIG. 4 indicates a convenient physical division point between a user's computer and a shared server computer.

Figure 5:
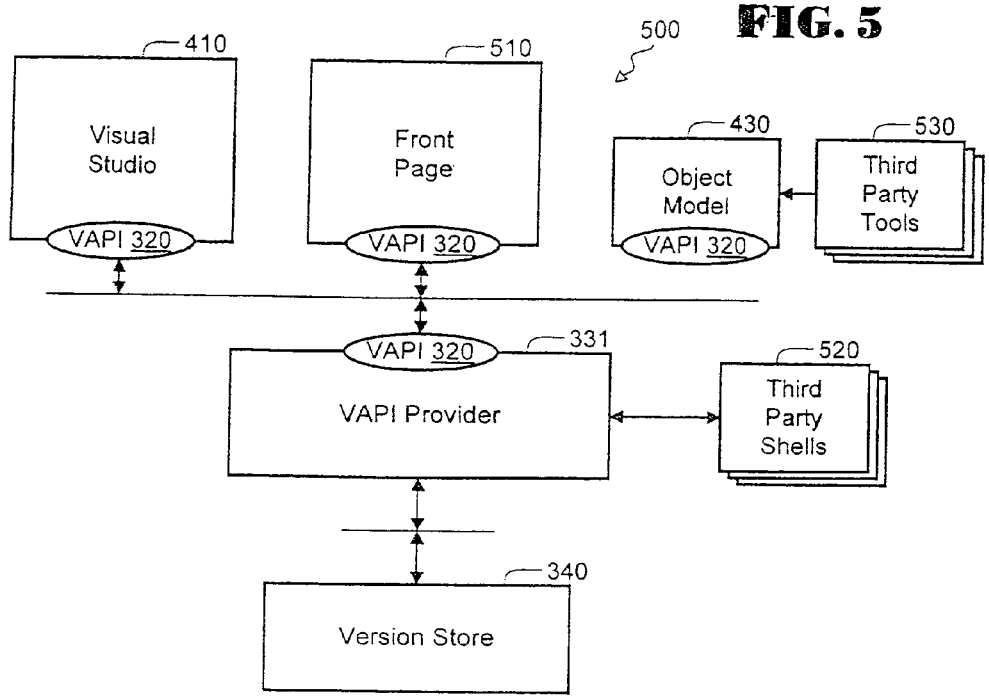
FIG. 5 shows the system of FIG. 3 from the viewpoint of a service provider.

FIG. 5 presents a versioning system 500 from the viewpoint of a typical VAPI-compliant service provider such as 331, FIG. 3. Above interface 320, a program such as provider 331 can be joined by other products 510 that use the same interface for different purposes. For example, if program 410 is a development suite such as Visual Studio® from Microsoft Corp., then program 510 might be the Front Page® authoring tool from Microsoft Corp. for developing pages for the World Wide Web. That is, multiple high-level application programs for different purposes can access the versioning service providers by complying with the VAPI interface 320. Because the embodiment described above uses the full-featured OLE DB interface, assuring compliance is relatively easy to achieve.

Third-party developers can write shells 520 for provider 331 that differ from the shells originally offered with the providers. Such shells might have different user dynamics, additional or modified functions, customizations for particular users, and similar features. Object model 430 can be supplied with the system to provide an API aimed at less sophisticated users for developing their own application programs and tools. Alternatively, tools can be written directly to VAPI 320.

3. Specific Service Providers

Versioning systems typically have separate components that provide services such as document editors for creating and modifying individual documents, query processors for locating documents, and merge engines for combining documents. The present invention accommodates service providers of conventional types if they are constructed according to the architecture described above. In addition, however, the extensible architecture permits third-party providers to offer entirely new functions as well.

Any system that supports parallel development by multiple groups of people requires a merge service for combining multiple documents while identifying and/or resolving any conflicts among them. (This function is also called "differencing," and these terms are used interchangeably.) In the present architecture, conflicts can occur anywhere within the system. Efficiency often dictates that a merge should be performed at different locations in the system. Thus, for example, a merge could take place in a versioning store, in a service provider, or within the client itself. However, merging at multiple places within the system can only happen in an extensible architecture that is neutral as to merge location. The present architecture abstracts both the type of merging that takes place and the time and location of the merge operation.

A merge returns a blob or arbitrary lump of data representing the merge results. The result document is typed to indicate which merge algorithm created it. One of several type-specific user interfaces can then be selected for displaying the results to a user for conflict resolution, if necessary. Even though the content of the result is opaque to the particular system component where the merge occurred and to the version store where the document resides, the single-interface architecture of the present system permits any component to route the document to a standard or custom plug-in merge engine that understands the file format of the document and the information within it.

Figure 6:
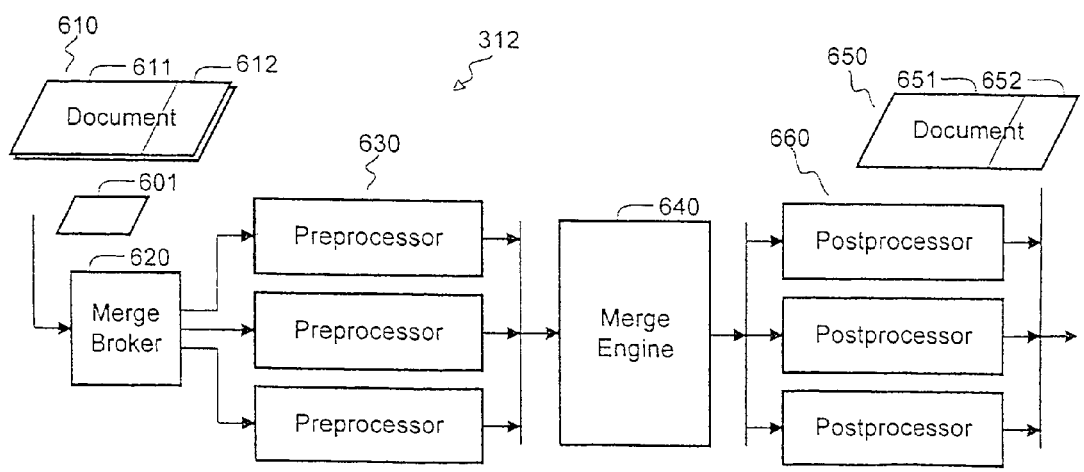
FIG. 6 is a block diagram of a merge subsystem useful with the system of FIG. 3.

FIG. 6 is a diagram of an architecture for a merge subsystem 312 for a versioning system that permits merge operations at multiple points. The component that desires to begin a merge operation calls a merge broker 620. Merging occurs in three phases: pre-processing, merge engine processing, post-processing. Merge preprocessors 630 are programs that modify the input data stream. For example, a preprocessor could extract information such as keywords and/or convert character codes, say from UTF8 to Unicode. Merge engine 640 is responsible for combining the inputs. Postprocessors 660 are components that run on the merge blobs to perform special processing or to automatically fix conflicts. The processed result document 650 a particular format and interfaces to the identified differences, is then returned to the calling program. Preprocessors and postprocessors are not necessarily symmetric. A preprocessor is specific to a certain type of data, and a postprocessor is specific to the output format of a given merge engine. That is, the difference between two specific versions is what is merged, so that a merge engine must allow for different blob input formats.

Upon invocation of a merge operation, broker 620 receives specifications of the documents to be merged, and optionally a desired format for the output merged document. The broker determines an overall merge plan or strategy, including which preprocessor 630 to run, which merge engine 640 to employ, and which postprocessor 660 to run. In the high-function development systems contemplated, multiple preprocessors might be required in order to convert documents in many different formats to those accepted by a desired merge engine, enhanced merging capabilities might require different engines, and processing different output formats and keyword sets can require different postprocessors. The plan might invoke multiple components of the same type, such as multiple preprocessors, say to convert the formats of two different input documents to yet a third format for a merge engine that accepts neither of the input formats. After selecting the participants, the broker orchestrates the execution of the merge plan. The standard interface set, object attributes and types provided by the invention allow these components to be mixed and matched in any desired combination.

The architecture of merge subsystem 312600 312 supports the notion of a collection of merge blobs. Documents used with the invention can be explicitly typed, as mentioned earlier. A single document might carry complex information, having multiple types—for example, both content 611 and properties 612. Changes to a file during a merge could produce conflicts both in the content of the merge result and in its properties. Thus a merge collection can contain both a content merge blob 651 and a property merge blob 652. Complex types can be returned in the result, as well as a composite of other merge data. A calling program can request reports as to differences, recommendations for merging, or automatic merging. The versioning architecture allows for the promotion of version deltas, that is, moving individual changes to a file between different versions of the file in the store. Because documents from different namespaces can participate in merge operations, the architecture also manages namespace merging.

FIG. 7 shows a process 700 for merging with the system of FIG. 6. In block 710, merge broker 620 receives a call, including the parameters and files discussed above. In block 711, the broker selects one (or possibly none) of the preprocessors 630, usually based upon its file type or format. The selected preprocessor modifies the input stream in block 720. Block 730 actually merges the files, optionally creating content and properties merge blobs in blocks 731 and 732. Block 733 selects one or more of the postprocessors 640, usually based upon factors such as the preprocessor used and the output file type. Blocks 740 then postprocess the merged documents and/or blobs, and return output document 650 to the calling component in block 741.

Files being merged can contain keyword expansions. It is therefore important to provide a mechanism by which keyword-expansion conflicts can be masked. In addition to the inputs listed above, callers can also identify a keyword domain that is appropriate for a merge input document. Broker 620 employs this information to automatically invoke domain-specific preprocessors 620 and postprocessors 660. A keyword preprocessor reduces keywords to a canonical form, and saves the appropriate expansion data. For example, $Foo: sdjhd$ would be reduced to $Foo: $. The keyword post-processor introduces keyword values back into the data stream in a non-conflicting way. This allows the result to include keyword expansion without having to involve the server.

Keyword expansion is the process by which files are augmented with special tags that contain well-defined information. For example, the version history of a document can be embedded in the document. As in the sample tag in the previous paragraph, a tag usually begins and ends with a reserved symbol (such as "$") that marks its boundaries. A symbol or text string ("Foo:") designates the type of tag. The remainder of the tag ("sdjhd") represents data of a type expected by the particular designator. Tags are usually processed in a store-specific way, and frequently include store-specific data. The present versioning architecture is capable of supporting multiple stores such as 340 within a single system. Therefore, it may include support for abstracting or generalizing keyword expansion.

Figure 8:
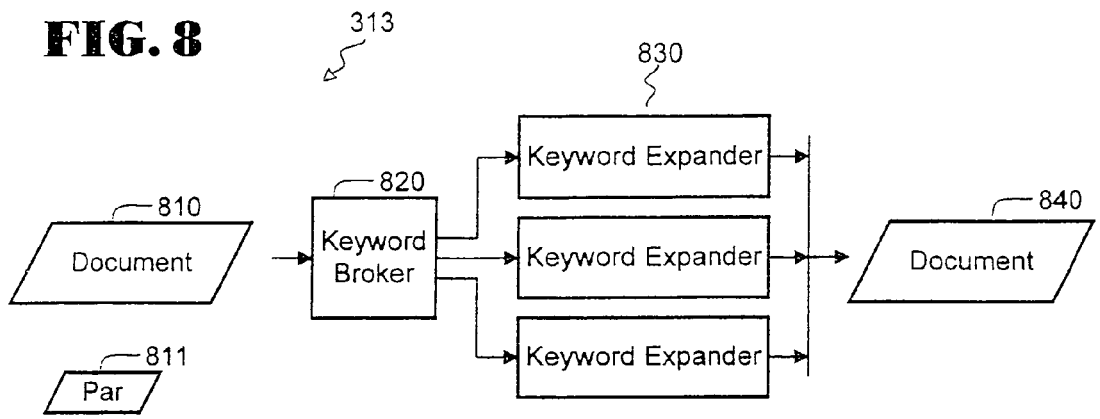
FIG. 8 is a block diagram of a keyword-expansion subsystem useful with the system of FIG. 3.

FIGS. 8 and 9 show an architecture for a keyword expansion subsystem 313, and its operation. When a component of system 300, FIG. 3, requests an expansion for a document 810, FIG. 8, it actually calls an expansion broker 820 in block 910, FIG. 9. Callers can use an enumerator to search the registered expanders and their associated keyword domains, block 911, and then pass a parameter 811 in block 912 identifying which set or domain of keywords apply to the document. This allows keyword expansion to happen anywhere in the entire system. Broker 820 receives the call at 920 and selects one of a number of keyword expanders 830 in block 921, in response to the file type or keyword domain. A keyword expander is a replaceable component for processing keywords at block 930. The extensible versioning architecture allows the definition of multiple keyword expanders, each associated with a specific domain of keywords.

Although keyword expansion typically occurs in a store 340 on a server such as 181 or 191, FIG. 1, it is possible that some keywords are only known on the client computer 120. If block 940 determines that this is the case, the store informs the client at block 950 that client-side keyword expansion is required. Block 951 then causes a client 310 or 410 to call generic keyword services as at 412 to perform the expansion 970, passing a domain identifier at 952. The service receives the call at 960, and expands the keywords at 970, using the type of keyword processor required by the domain parameter. The server may also specify particular keywords and, optionally, values for those keywords.

Figure 10:
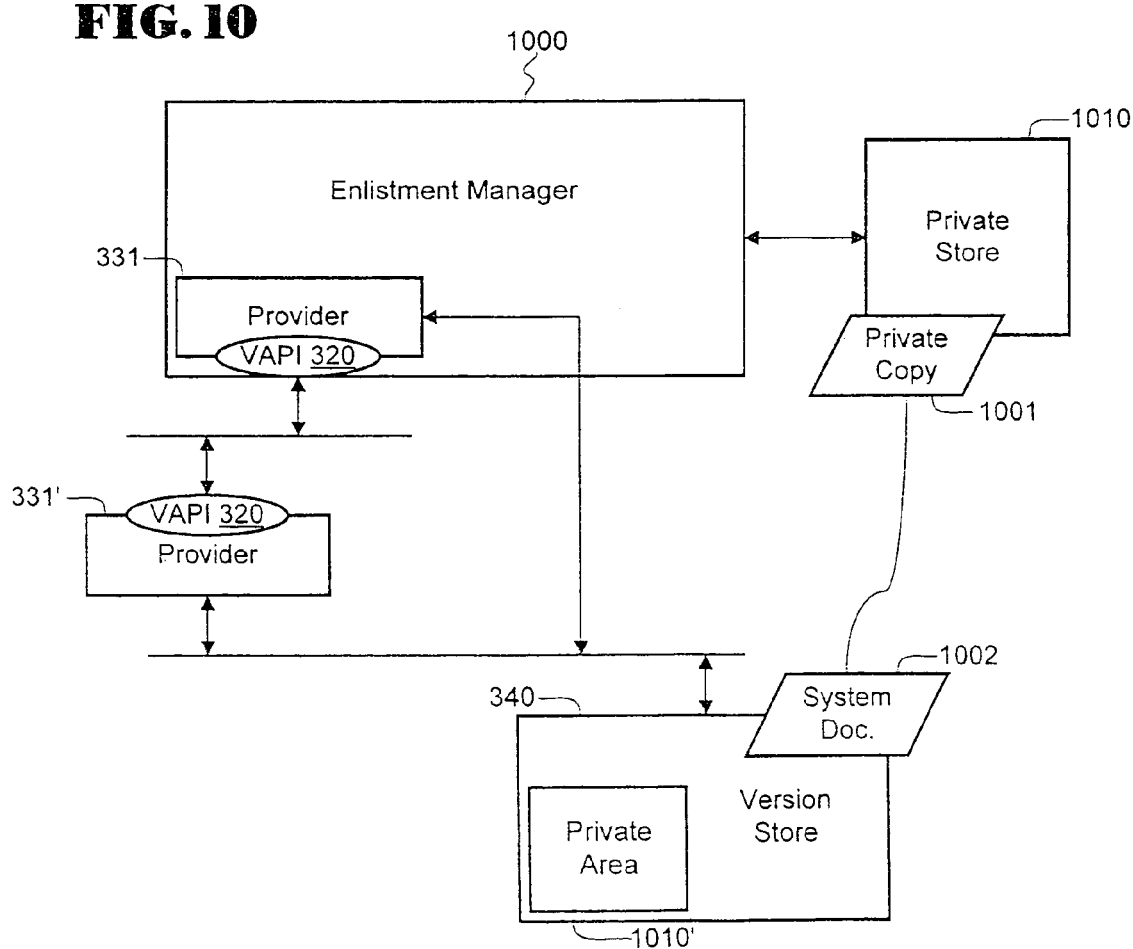
FIG. 10 is a block diagram showing an enlistment manager for the system of FIG. 3.

FIG. 10 shows another kind of version service, an enlistment manager 1000. Some systems permit development team members to store and modify their own private copies 1001 of source files 1002 to build from. A set of such isolated copies is called an enlistment. It can be thought of as a smart folder that knows how to perform a number of functions, including— tracking the versions downloaded to it,
 tracking namespace changes,
 managing a relationship, such as an isolated set of changes to a master document, with version store 340,
 providing off-line support functions and cached data when a developer is not logged into the system,
 offering a staging area for document changes,
 storing object properties locally, and
 keeping local documents that are not in the version store on the server.

Enlistment manager 1000 offers these functions, and has a superset of the functionality of a direct service provider 330, FIG. 3. It can reside anywhere in the system; it can be implemented as a component associated with a service provider, indicated at 331, or have a service provider 331' embedded within it. One embodiment might employ a client file system, whereas another might use a server location, for example. Enlistment might ot might not track versions themselves.

A private store 1010 holds the enlistments. The private store can be realized in several ways. It can, for example, employ a local file system of a client computer. Alternatively, it could form a private area 1010' in the overall version store 340. An enlistment manager 1000 can be constructed with a number of characteristics. It supports the ability to synchronize an enlistment to any point in time (i.e., version), both forward and backward. It can switch the store or branch upon which it is based to another store or branch. Enlistments are transportable. A project that is stored on a removable medium, for example, continues to function when moved to a different computer with access to the version store. Enlistments may support atomic transactions, so that the enlistment cannot be left in an inconsistent state. For instance, a "get" operation on multiple files or documents replaces the target files only if and when all the requested files are obtained, and always rolls back the entire transaction if an error is encountered for any of the files. An enlistment manager supports the synchronization of only portions of a namespace, and excludes ("ghosts") folders or files that are not required for the enlistments. Each of above and other desirable characteristics is known in the art. For example, database systems commonly support atomic transactions. Thus, a programmer can construct an enlistment manager according to the invention that includes whichever of these characteristics that may be desired.

CONCLUSION

The present invention offers an extensible software-development or versioning system architected as modules for performing individual development functions. Because the individual modules have an interface compatible with each other, modules not in the original system can be added to provide more services, or substituted for one or more of the original modules. The architecture of this system supports the performance of actions such as document merging and keyword expansion at any location in the system. Further, the interfaces operate upon documents and files as objects in an object space, rather than in one or more name spaces.

The invention claimed is:

1. A system for managing versions of software under development, versions of the software being stored in a version store including a plurality of development documents related to a software development project, the system comprising:
   a database that implements the version store; and
   a client processing system including a processor for receiving commands from a user and communicating the commands to one or more of a plurality of service providers for execution upon one or more of the development documents from the version store, wherein each of the plurality of service providers performs a different development function, wherein the client processing system and the plurality of service providers have a mutually compatible versioning application program interface for communicating the commands, and wherein the client processing system employs:
   a merge subsystem for providing merge/differencing services that combine multiple versions of a document to form a single document, wherein the merge subsystem includes a plurality of merge preprocessor modules that modify an input stream, a merge engine that combines the outputs of the preprocessor modules into a single document, a plurality of postprocessors that process the single document from the merge engine and provide the processed single document to the version store as a development document, and a merge broker that determines a merge plan including selection of one or more of said plurality of preprocessors and one or more of said plurality of postprocessors for use in creating said development document; and
   a keyword subsystem for providing keyword-expansion services that provide information tags to the development document, the information tags including version store-specific data within defined boundaries, said version store-specific data including content having a predetermined format supportive of version storing within defined boundaries, wherein the keyword subsystem is configured to:
      receive a client request for keyword expansion using at least one of a plurality of keyword expanders;
      select at least one of the keyword expanders in response to the client request;
      pass to the selected at least one keyword expander a parameter identifying which set or domain of keywords to apply to the development document, whereby the information tags may be provided to the development document to create a keyword expanded development document anywhere in the system; and
      provide the keyword expanded development document with said information tags including said version store-specific data including content having said predetermined format supportive of version storing within said defined boundaries to the version store.

2. The system of claim 1 where all of the service providers and the client are replaceable by a third party.

3. The system of claim 1 where each of the application program interfaces include a set of methods.

4. The system of claim 3 where at least one of the service providers implements less than all of the methods in the set.

5. The system of claim 3 where each of the application programming interfaces include at least a subset of an Object Linking and Embedding database.

6. The system of claim 1 further including an object model also exposing the mutually compatible versioning application program interface.

7. The system of claim 1 further including a command-line utility for passing user commands to the service providers through the mutually compatible versioning application program interface.

8. The system of claim 1 where the version store and the client processing system are physically located in different computers.

9. A method for managing versions of software under development, versions of the software being stored in a version store including a plurality of development documents related to a software development project, the method comprising:
   implementing the version store as a database;
   receiving, in a client processing system, commands from a user and communicating the commands to one or more of a plurality of service providers for execution upon one or more of the development documents from the version store, wherein the service providers are located in one or more computers and perform different development functions, and wherein the client processing system and the service providers employ a set of mutually compatible interfaces implemented as application program interfaces for communicating the commands;

said client processing system providing merge/differencing services that combine multiple versions of a document to form a single document in accordance with a merge plan implemented by a merge broker and provide the single document to the version store as a development document;

said client processing system receiving a client request for keyword expansion using at least one of a plurality of keyword expanders that provide information tags to the development document, the information tags including version store-specific data within defined boundaries, said version store-specific data including content having a predetermined format supportive of version storing within defined boundaries;

selecting at least one of the keyword expanders in response to the client request;

said client processing system passing to the selected at least one keyword expander a parameter identifying which set or domain of keywords to apply to the development_document, whereby the information tags may be provided to the development document to create a keyword expanded development document anywhere in the client processing system; and the client processing system providing the keyword expanded development document with said information tags including said version store-specific data including content having said predetermined format supportive of version storing within said defined boundaries to the version store.

10. The method of claim 9 where all of the service providers and the client are replaceable by a third party.

11. The method of claim 9 where each of the application program interfaces include a set of methods.

12. The method of claim 11 where at least one of the service providers implements less than all of the methods in the set.

13. The method of claim 11 where each of the application programming interfaces include at least a subset of a Object Linking and Embedding database.

14. The method of claim 9 further comprising exposing the mutually compatible interfaces via an object model.

15. The method of claim 9 further comprising passing user commands to the service providers through the mutually compatible interfaces via a command-line utility.

16. The method of claim 9 where the database and the client are physically located in different computers.

* * * * *